US012728148B2

(12) United States Patent
Commeurec et al.

(10) Patent No.: US 12,728,148 B2
(45) Date of Patent: Sep. 8, 2026

(54) NON-RINSED VETERINARY COMPOSITIONS

(71) Applicant: Ceva Santé Animale, Libourne (FR)

(72) Inventors: Emeline Commeurec, Libourne (FR); Nadége Maubert, Libourne (FR)

(73) Assignee: CEVA SANTE ANIMALE, Cedex (FR)

( * ) Notice: Subject to any disclaimer, the term of this patent is extended or adjusted under 35 U.S.C. 154(b) by 957 days.

(21) Appl. No.: 17/780,764

(22) PCT Filed: Nov. 27, 2020

(86) PCT No.: PCT/EP2020/083608
§ 371 (c)(1),
(2) Date: Nov. 16, 2022

(87) PCT Pub. No.: WO2021/105340
PCT Pub. Date: Jun. 3, 2021

(65) Prior Publication Data

US 2023/0127281 A1 Apr. 27, 2023

(30) Foreign Application Priority Data

Nov. 28, 2019 (EP) .................................... 19212297

(51) Int. Cl.
*A61K 36/8968* (2006.01)
*A61K 9/00* (2006.01)
*A61K 31/164* (2006.01)
*A61K 47/20* (2006.01)

(52) U.S. Cl.
CPC ........ *A61K 36/8968* (2013.01); *A61K 9/0017* (2013.01); *A61K 31/164* (2013.01); *A61K 47/20* (2013.01)

(58) Field of Classification Search
CPC ...................................................... A61P 17/00
See application file for complete search history.

(56) References Cited

U.S. PATENT DOCUMENTS

2006/0074029 A1 4/2006 Leece
2006/0275235 A1 12/2006 Takeda et al.
2010/0239695 A1* 9/2010 Vielhaber ............... A61P 29/00 424/765
2011/0097281 A1* 4/2011 Neubourg ............. A61K 47/10 424/46
2015/0147286 A1* 5/2015 Barrera ................. C11D 3/162 424/70.122
2015/0297652 A1 10/2015 Balaraman
2018/0072817 A1* 3/2018 Lin ....................... A61K 8/466
2019/0110967 A1 4/2019 Chiou

FOREIGN PATENT DOCUMENTS

CN 109602627 A 4/2019
JP 2005126329 A 5/2005
JP 2013521259 A 6/2013
WO 2004099258 A1 7/2006
WO 2011107522 A2 9/2011
WO WO-2017121965 A1 * 7/2017 .......... A61K 31/702

OTHER PUBLICATIONS

Ebner Fritz et al. “Topical use of dexpanthenol in skin disorders” American Journal of Clinical Dermatology, ADIS, US, vol. 3, No. 6, Jan. 1, 2002 (Jan. 1, 2002), pp. 427-433 DOI: 10.2165/00I 2807I-200203060-00005 ISSN: 1175-0561, XP009181863.
Unknown. “Pentavitin binds to keratin in skin to keep the moisture balance” Jan. 1, 2009 (Jan. 1, 2009), pp. 1-2, Retrieved from the Internet: https://www.cosmeticsonline.com.br/subcategorias/S UB19_ DSM%20PENTAVITIN.pdf.
Yakugaku Zasshi, “Surfactant-induced Itching and the Involvement of Histamine Released from Keratinocytes”, 132(11); 1225-1230 (2012) The Pharmaceutical Society of Japan.
Office Action for Australian Patent Application No. 2020392433 mailed Sep. 16, 2025.
“Perfection Difference Cream”, MINTEL GNPD, Available from the Internet: https://www.gnpd.com/sinatra/recordpage/3696789/, Published Jan. 2016, Last Retrieved Sep. 8, 2025.
“Firming & Moisturizing Mask”, MINTEL GNPD, Available from the Internet: https://www.gnpd.com/sinatra/recordpage/4355519/, Published Oct. 2016, Last Retrieved Oct. 8, 2025.

* cited by examiner

*Primary Examiner* — Gina C Justice
(74) *Attorney, Agent, or Firm* — Wood, Phillips, Katz, Clark & Mortimer

(57) ABSTRACT

The invention relates to the veterinary field and, more particularly, non-rinsed compositions comprising an active ingredient obtained from *Ophiopogon japonicus*, panthenol and saccharide isomerate, for non-human mammals. The invention also relates to a method for treating the coat of non-human mammals by applying said non-rinsed compositions to the coat and/or the skin.

13 Claims, No Drawings

NON-RINSED VETERINARY COMPOSITIONS

OBJECT OF THE INVENTION

The present invention relates to the veterinary field and, more particularly, to non-rinsed compositions comprising an active ingredient obtained from *Ophiopogon japonicus*, panthenol and saccharide isomerate, intended for non-human mammals. It also relates to a method for treating the coat of non-human mammals by applying said compositions to the coat and/or the skin.

TECHNICAL BACKGROUND OF THE INVENTION

The active ingredient obtained from *Ophiopogon japonicus*, and the hydrating effect thereof or the effect thereof for reinforcing the barrier function of human skin has been described in the patent EP2271311. The use of said active ingredient for treating atopic dermatitis in animals and humans has been described in the patent application WO2017/121965.

The skin and the coat of non-human mammals protect said mammals from external aggressions. Their upkeep is therefore very important for the well-being, and indeed the health, of non-human mammals. It is in particular important to preserve and protect the good functioning of the cutaneous barrier function. However, this can be altered by external aggressions such as heat, cold, humidity, etc.

A veterinary product intended for treating the skin or the coat must therefore be effective for preserving the barrier function, without causing irritation or any other skin disorder.

Furthermore, bacteria exist which may be pathogenic or become pathogenic if they are too numerous, such as the staphylococcaceae, for dogs and/or cats, which require particular treatments in view of their reduction or elimination. These staphylococcaceae are represented primarily by *S. pseudintermedius.*

There is therefore a need for compositions for non-human mammals, and in particular for dogs and cats, which make it possible to preserve, or indeed improve, the barrier function of the skin and of the coat, and which confer a good hydrating effect.

There is also a need to preserve the bacterial flora which is beneficial to the mammals, while reducing, or indeed eliminating, the pathogenic bacteria.

There is also a need for a lasting effect, by direct application to the skin or the coat of the non-human mammals.

SUMMARY OF THE INVENTION

In this context, the applicant is proposing a new non-rinsed veterinary composition comprising an active ingredient obtained from *Ophiopogon japonicus*, panthenol and saccharide isomerate.

The present invention thus relates to a non-rinsed veterinary composition comprising an active ingredient obtained from *Ophiopogon japonicus*, panthenol and saccharide isomerate, which is intended to be used as a product for treating a non-human mammal, in particular a dog or a cat.

A further object of the invention thus relates to a method for treating the skin and/or the coat of a non-human mammal, and in particular a dog or a cat, by applying the composition of the present invention to the skin and/or the coat of said mammal.

A further object of the invention relates to the use of a composition as defined in the present application, or a method using said composition for reducing and/or preventing the presence of pathogenic bacteria and/or the formation and/or the adhesion of pathogenic bacteria biofilms in the case of a non-human mammal, such as a dog or cat.

DETAILED DESCRIPTION OF THE INVENTION

The invention as described in the present application relates to a non-rinsed veterinary composition comprising an active ingredient obtained from *Ophiopogon japonicus*, panthenol and saccharide isomerate.

"Non-rinsed composition" means a composition which is formulated so as to remain, following application, on the skin or the coat of non-human mammals. The non-rinsed composition is applied directly to the skin or the coat, and does not need to be subsequently eliminated by rinsing with water. The non-rinsed composition is advantageously in the form of a mousse.

*Ophiopogon japonicus* is a perennial, low and abundant herbaceous species having rhizomes, from the family of the Liliaceae. It is cultivated as an ornamental covering plant having tuberous rhizomes, and has a very large number of uses in traditional Chinese medicine.

The species is originally from Japan and Korea, and is also cultivated in Vietnam and in China, in particular in Sichuan, Zhejiang and Hubei provinces. It is also referred to as "Muguet du Japon" in France, and "Mondo grass," "Fountain plant," "Monkey grass" or "Dwarf lilyturf" in English. The tuberous root is of a length of a few centimeters; it is light yellow to yellow-brown in color on the outside, having longitudinal wrinkles. Its smell is slight, and its taste slightly sweet and mucilaginous. In traditional Chinese medicine, the root is known to "feed the Lungs and the Yin, to feed the Stomach and produce Fluids, to remove the Heat from the heart, and to soothe the Spirit." The main therapeutic indications relate to dry coughs, sore throats, insomnia, irritability, constipation and diphtheria, according to the 16th edition of the Japanese Pharmacopeia.

The roots of *Ophiopogon japonicus* originate from strains cultivated in China and Vietnam. Extracts of *Ophiopogon japonicus* are known in cosmetics for the skin, in particular in the patent EP2271311, as a moisturizer by action on the rate of NMF (Natural Moisturizing Factors) and on the formation of tight junctions of the cutaneous layers. The application WO 2017/121965 also describes that extracts of *Ophiopogon japonicus* can be used for treating atopic dermatitis.

Within the meaning of the invention, "active agent" or "active ingredient" or "extract" means at least one molecule, preferably a set of molecules, having an effect on the cells of the skin.

Within the meaning of the invention, "active agent obtained from *Ophiopogon japonicus*" means any molecule or mixture of molecules obtained from *Ophiopogon japonicus*. They may be native molecules of the plant, or molecules obtained by any kind of transformation of native molecules of the plant, for example by hydrolysis. The active agent according to the invention is preferably a hydrolysate.

"Hydrolysate" means any extract originating from *Ophiopogon japonicus* which is obtained by means of a method comprising at least one step of enzymatic or chemical hydrolysis of *Ophiopogon japonicus*, preferably at least one step of enzymatic hydrolysis. "*Ophiopogon japonicus*"

means all or part of the plant. It may be the entire plant, or a part of the plant. It is preferably tubers of *Ophiopogon japonicus*.

"Oligosaccharides" means oligomers formed of a number of monosaccharides by glycosidic bonding, the number of units of monosaccharides being less than 25 units.

"Polysaccharides" means polymers formed of a plurality of simple sugars which are interconnected by osidic bonding, the number of units of monosaccharides being greater than 25 units.

The active agent obtained from *Ophiopogon japonicus*, used in the composition according to the invention, is preferably an active agent obtained from *Ophiopogon japonicus* comprising sugars. Even more preferably, it comprises fructosans, and more particularly it comprises at least 57% fructosans by weight with respect to the total weight of sugars of the active agent, even more preferably at least 80%. The fructosans are polysaccharides made up of fructose and glucose. The sugars containing the active agent are preferably made up of 45 to 80% fructose, 20 to 50% glucose, and 0 to 5% galactose. Said sugars may be in the form of monomers, oligomers and polymers. Predominantly, the sugars contained in the active agent are oligo- and polysaccharides of molecular weights of less than 400 kDa, in the form of fructosans. Thus, the active agent according to the invention preferably comprises oligo- and polysaccharides of molecular weights of less than 400 kDa, in the form of fructosans, representing at least 57 wt. % of the sugars present in the active agent. According to a particularly suitable variant, the active agent is obtained from tubers of *Ophiopogon japonicus*.

According to an embodiment, the active agent used for preparing the composition according to the invention is present in the form of a powder, in particular a clear-colored powder, and has at least one of the following features, preferably all:

- an amount of dry matter of between 900 and 1000 mg/g, or
- a sugar content of between 500 and 800 mg/g, i.e. at least 50% sugars by weight with respect to the weight of dry matter.

The amount of dry matter may be measured by passing a sample into a sterilizer at 105° C. until a constant weight is achieved.

The overall content of sugars may be determined by the DUBOIS method, on a range of fructose (Dubois M. et al., Analytical chemistry, 28, 3, 350-356, 1956). The characterization of the molar mass of the carbohydrates present in the active agent of the present invention may be achieved by an HPLC method and by metering of simple sugars by ionic liquid chromatography.

The molar masses of the carbohydrates are evaluated by comparing the retention times of the peaks detected in the samples of the active agent with the retention times of standards injected previously.

The operating conditions are preferably as follows:

Apparatus: Agilent 1100 Series HPLC

Columns: PL aquagel-OH C60, C40, C30 columns having a pre-column of the same characteristics Elution mode: isocratic Mobile phase: Buffer NaN030.3 M+NaH2P04-2H20 0.01 M pH 7

Detection wavelengths: UV 254 nm and 280 nm

The active agent according to the invention is preferably an active agent obtained in aqueous medium from tubers of *Ophiopogon japonicus*. "Obtained in aqueous medium" means a medium containing mainly water, or a basic or acidic aqueous medium. In particular, it is not an oil or an essential oil.

The active agent according to the invention is preferably a hydrolysate of *Ophiopogon japonicus*, preferably an enzymatic hydrolysate.

According to a particularly suitable variant, the active agent according to the invention is a hydrolysate of *Ophiopogon japonicus*, preferably an enzymatic hydrolysate of tubers of *Ophiopogon japonicus*.

In particular, the active agent which can be used according to the invention can be obtained by implementing the following steps:

- solubilization of powder of *Ophiopogon japonicus* (preferably of tubers) in water at the rate of at least 50 g/l,
- at least one enzymatic hydrolysis of sugars,
- separation of the soluble and insoluble phases, for example by settling,
- enzymatic inactivation by heat treatment of the soluble phase.

The enzymatic inactivation may be followed by one or more steps of filtration and/or concentration. The active agent may be obtained in liquid form or in the form of powder, by atomization or lyophilization. It is preferably atomized, in the presence of an atomization additive of the maltodextrin type, and used in powder form.

The parameters of the various steps have to be adjusted in order to obtain active agents having the features of the invention, in particular the presence of fructosans having a molecular weight of less than 400 kDa.

According to a preferred embodiment, the active agent is atomized using maltodextrin; it is thus present in powder form (before formulation into the composition according to the invention).

The composition according to the invention advantageously comprises at least 0.1 wt. %, with respect to the total weight of the composition, active agent obtained from *Ophiopogon japonicus*, according to the present invention, preferably between 0.1 and 1 wt. %, with respect to the total weight of the composition, and more particularly between 0.2 and 0.6 wt. %, with respect to the total weight of the composition.

The composition according to the invention comprises panthenol. The composition advantageously comprises at least 0.1 wt. % panthenol, with respect to the total weight of the composition, preferably from 0.1 wt. % to 1 wt. %, and more particularly from 0.3 wt. % to 0.8 wt. %.

The composition according to the invention comprises saccharide isomerate.

The saccharide isomerate is a hydrating active ingredient. It contains mainly fructose and glucose. The preparation of said active ingredient is described in particular in the U.S. Pat. No. 3,578,655. The saccharide isomerate is in particular marketed under the name "PENTAVITIN®" by the company DSM.

The composition advantageously comprises at least 0.1 wt. % saccharide isomerate, with respect to the total weight of the composition, preferably from 0.1 wt. % to 1 wt. %, and more particularly from 0.3 wt. % to 0.9 wt. %.

The composition preferably comprises one or more surfactant(s).

Said surfactant is preferably selected from the amphoteric surfactants of the betaine type, the carboxylic anionic surfactants, the alkyl(poly)glucoside nonionic surfactants, and the mixtures thereof.

The amphoteric surfactants of the betaine type are preferably selected from the alkyl(C8-C20)betaines, the alkyl (C8-C20)amidoalkyl(C1-C8)betaines, the alkyl(C8-C20) amidoalkyl(C1-C8)sulfobetaines, the alkyl(C8-C20) amidoalkyl(C1-C6)hydroxysulfobetaines, the sulfobetaines and the hydroxysulfobetaines. By way of example, particularly the compounds classified under the designations coco betaine, lauryl betaine, cetyl betaine, coco/oleamidopropyl betaine, capryl/capramidopropyl betaine, cocamidopropyl betaine, palmitamidopropyl betaine, stearamidopropyl betaine, cocamidoethyl betaine, cocamidopropyl hydroxysultaine, oleamidopropyl hydroxysultaine, coco hydroxysultaine, lauryl hydroxysultaine, coco sultaine, alone or in mixtures, can be cited.

In particular, said at least one amphoteric surfactant of the betaine type is selected from the alkyl(C8-C20)amidoalkyl (C1-C6)betaines, the alkyl(C8-C20)amidoalkyl(C1-C6) sulfobetaines (also referred to as alkyl(C8-C20)amidoalkyl (C1-C6)sultaines), the alkyl(C8-C20)amidoalkyl(C1-C6) hydroxysulfobetaines (also referred to as alkyl(C8-C20) amidoalkyl(C1-C6)hydroxysultaines). The amphoteric surfactant of the betaine type is preferably selected from the alkyl(C8-C20)amidoalkyl(C1-C6)betaines. It is more specifically capryl/capramidopropyl betaine (in particular marketed by the company Evonik under the trade name "Tego® Betain 810").

More specifically, the composition may comprise capryl/capramidopropyl betaine. The amount of capryl/capramidopropyl betaine may be between 0.1 and 5 wt. %, preferably between 0.3 and 3 wt. %, with respect to the total weight of the composition.

According to the invention, the carboxylic anionic surfactants are anionic surfactants having at least one carboxylic function (—COOH), optionally in the form of a salt ($—COO^-$).

The anionic surfactants of the carboxylic type can in particular be selected from the alkyl D-galactoside uronic acids and the salts thereof, the alkyl (C6-C24) ether carboxylic polyoxyalkylene acids, the alkyl (C6-C24) aryl ether carboxylic polyoxyalkylene acids and the salts thereof, the alkyl (C6-C24) amido ether carboxylic polyoxyalkylene acids and the salts thereof, in particular those comprising 2 to 50 alkylene, in particular ethylene, oxide groups such as the compounds proposed by the company KAO under the names AKYPO, the acyl (C6-C24) sarcosinates and the salts thereof, the acyl (C6-C24) lactylates and the salts thereof, and the acyl (C6-C24) glutamates. It is also possible to use the esters of carboxylic alkyl(C6-C24)polyglycosides such as the acetate alkyl glucosides, the citrate alkyl glucosides, and the tartrate alkyl polyglycosides. Such products are in particular marketed under the names Eucarol APG/EC and Eucarol APG/ET by the company Lamberti, and Plantapon LGC SORB by the company Cognis.

The salts are in particular selected from the alkaline salts, in particular of sodium, the ammonium salts, the amine salts, the aminoalcohol salts such as triethanolamine or monoethanolamine, and the magnesium salts.

Preferably the acyl (C6-C24) sarcosinates and the salts thereof are used.

More specifically, the composition may comprise sodium lauroyl sarcosinate, in particular marketed by the company Seppic under the trade name Oramix® L30. The amount of sodium lauroyl sarcosinate may be between 0.1 and 5 wt. %, preferably between 0.3 and 3 wt. %, with respect to the total weight of the composition.

The alkyl(poly)glucoside nonionic surfactants can in particular be decyl glucoside, lauryl glucoside, cocoyl glucoside or capryl/caprylyl glucoside. The composition according to the invention preferably comprises capryl/caprylyl glucoside.

More specifically, the composition may comprise capryl/caprylyl glucoside, in particular marketed by the company Seppic under the trade name Oramix® CG110. The amount of capryl/caprylyl glucoside may be between 0.1 and 5 wt. %, preferably between 0.3 and 3 wt. %, with respect to the total weight of the composition.

The surfactant is preferably selected from sodium lauroyl sarcosinate, capryl/capramidopropyl betaine, caprylyl/capryl glucoside, or the mixture thereof.

The surfactant is advantageously present in the composition according to the invention in amounts of from 0.1 to 10 wt. %, with respect to the total weight of the composition, preferably from 0.1 to 5 wt. %, and more particularly from 0.3 to 3 wt. %.

The composition according to the invention may comprise other compounds such as modified or unmodified guar gum. More particularly, the composition according to the invention comprises cationic galactomannan gums (which are described more particularly in the U.S. Pat. Nos. 3,589,578 and 4,031,307). Guar gums comprising cationic trialkylammonium groups can be cited. For example, guar gums are used which are modified by a salt (for example a chloride) of 2,3-epoxypropyl trimethylammonium. Such products are marketed in particular under the name JAGUAR® EXCEL by the company Solvay or SACI-CFPA. The modified or unmodified guar gums are advantageously present in the composition in amounts of between 0.05 and 0.2 wt. %, preferably between 0.05 and 0.15 wt. %, and at best between 0.08 and 0.13 wt. %, with respect to the total weight of the composition.

The compositions according to the invention may furthermore comprise agents which are beneficial for the skin or the coat. These ingredients are generally introduced into the composition in order to improve the touch qualities of the keratinic fiber of the coat or of the skin or indeed to promote the hydration thereof. The cationic polymers, the silicones and the emollients, such as the polyols, constitute, in this context, the most commonly used ingredients.

The composition according to the invention can advantageously comprise one or more ingredients selected from chlorhexidine digluconate, niacinamide, vegetable extracts such as oat extract, extract of Punica granatum, and one of the mixtures thereof.

The composition according to the invention may further comprise other compounds, in particular selected from the saccharides, oligosaccharides, hydrolyzed or non-hydrolyzed polysaccharides, modified or unmodified, amino acids, oligopeptides, peptides, hydrolyzed or non-hydrolyzed proteins, modified or unmodified, branched or unbranched fatty acids and alcohols, animal, vegetable or mineral oils or waxes, ceramides and pseudoceramides, hydroxylated organic acids, antioxidants, anti-free radical agents, cationic, anionic or nonionic polymers, soluble or dispersed, or a mixture of said compounds.

Of course, a person skilled in the art will be sure to select this or these possible additional compounds and/or their amounts in such a way that the advantageous properties intrinsically linked with the association according to the invention are not, or substantially not, altered by the intended addition(s).

Said additives are optionally present in the composition according to the invention in proportions which may be from 0.00001 to 30 wt. %, with respect to the total weight of the composition. The exact amount of each additive is easily determined by a person skilled in the art, depending on the type and function thereof.

The composition according to the invention is advantageously an aqueous composition. It may comprise water in amounts of from 50 to 98 wt. % with respect to the total weight of the composition, preferably from 60 to 98 wt. %, particularly from 70 to 98 wt. %.

The composition may be in the form of a lotion, a gel, a cream, or a mousse. The composition according to the invention is advantageously in the form of a mousse, in particular when it comprises the surfactant(s) described above. The mousse may be formed from a mixture of propellant air or gas, with the composition described above.

The composition, before distribution, may be packaged in a mousse dispenser, allowing distribution of said composition in the form of a mousse.

The dispenser may be an aerosol dispenser. This is generally formed by a metal or glass or plastics material container, said container being hermetically sealed and provided with a withdrawal device allowing the emergence of the product in the form of mousse. The withdrawal device generally comprises a plunger tube, a valve, and a diffuser provided with a nozzle. The dispenser comprises the composition according to the invention and a propellant gas. The propellant gas may be selected from nitrogen dioxide, nitrogen, dimethyl ether, butane, isobutane, propane, pentane, and the mixtures thereof.

According to another variant, the dispenser may be non-aerosol, of the pump type. The composition may be distributed from a container by means of a mechanical pump which is connected to a dispensing head, the passage of the composition into the dispensing head turning it into a mousse, at the latest in the region of the outlet orifice of said head.

The invention further relates to a veterinary treatment device for treating the skin and/or the coat of a non-human mammal, comprising:

- a composition containing the surfactant as described above; and
- a mousse dispenser, allowing distribution of said composition in the form of a mousse.

The invention also relates to a method for treating the skin and/or the coat of a non-human mammal, and in particular a dog or a cat, by applying the composition of the present invention to the skin and/or the coat of said mammal.

The invention also relates to the composition of the present invention for use in the treatment of the skin and/or the coat of a non-human mammal, and in particular a dog or a cat.

The compositions according to the invention are implemented by simple application to the non-human mammal, optionally by massage or friction using the hands. The applied composition does not need to be rinsed using water.

The method or the use according to the invention also makes it possible to be non-irritant, or indeed to reduce the irritation of the skin, which reduces the stress and provides an effect of well-being to the non-human mammal, in particular the dog or the cat.

The non-rinsed compositions according to the invention for non-human mammals, and in particular for dogs and cats, make it possible to preserve, or indeed improve, the barrier function of the skin and/or of the coat. In particular, the treated skin is supple and hydrated in a lasting manner, and has a good level of impermeability. The applied composition provides good reinforcement to the mechanical barrier of the skin, as well as a lasting residual hydrating effect. The compositions according to the invention for non-human mammals, and in particular dogs and cats, also makes it possible to reduce the presence of pathogenic bacteria or the development thereof, or to reduce and/or prevent the formation and/or the adhesion of pathogenic bacteria biofilms, the pathogenic bacteria being in particular *Staphylococcus aureus* and/or *Staphylococcus pseudintermedius.*

The compositions according to the invention also make it possible to preserve, or indeed improve, the silky appearance of the coat.

Moreover, the application of the non-rinsed composition onto the skin or the coat allows for lasting action of the composition applied.

Furthermore, when the composition is in the form of a mousse, it is easy to apply to the surface of the skin or the coat, in particular by massaging, which provides a relaxing effect. This ease of application allows for frequent use of the composition, which may be applied to the mammal several times per week.

A further object of the invention relates to the use of a composition as defined above, or a method using said composition, for reducing and/or preventing the formation and/or the adhesion of pathogenic bacteria biofilms, or for reducing the presence, on the skin or the coat, of pathogenic bacteria, such as *Staphylococcus aureus* and/or *Staphylococcus pseudintermedius*, in a non-human mammal, in particular a dog or cat.

Thus, the use of a composition as defined above, or a method using said composition, for reducing and/or preventing the formation and/or the adhesion of pathogenic bacteria biofilms, or for reducing the presence of pathogenic bacteria, can be achieved by application of a composition as defined above.

According to a particular embodiment of the invention, the non-human mammal is selected from the felids, the canines, and/or the equids, and in particular dogs and cats.

The term "approximately" will be understood by a person skilled in the art, and can vary to a certain extent, depending on the context in which it is used. If some uses of this term are not clear to a person skilled in the art, depending on the context "approximately" means plus/minus 10%, preferably plus/minus 5%, of the value indicated.

The values indicated in the intervals specified in the text must be included, unless otherwise stated.

According to the invention, the term "comprises" or "comprise" (and other comparable terms, for example "containing" and "including") is "open" and may be interpreted, in a general manner, such that the specific features mentioned, and all the optional, additional and non-specified features are included. According to specific embodiments, it may also be interpreted as an expression "essentially consisting in," which includes the specific features and any optional, additional or non-specified feature which does not materially affect the fundamental and new feature or features of the claimed invention, or as an expression "consisting in," where only the specific features are included, unless otherwise indicated.

According to the invention, the term "at least" means "one," "two," "three," or more.

Other aspects and advantages of the invention will appear from reading the following examples, which should be considered as illustrative and non-limiting.

The percentages indicated are by weight, unless otherwise stated.

EXAMPLES

The following compositions of tables 1 to 3 are prepared according to the conventional methods for preparing aqueous compositions. They are packaged in a pump bottle which distributes the composition in the form of mousse by profusion in air.

These compositions exhibit good application properties for application to the coat of a dog and cat, in particular by relaxing massage, facilitating frequent use, for example 3 times per week. The composition applied is in direct contact with the skin in a more lasting manner. They make it possible to improve the barrier function, to restore the microbial balance, and in particular to reduce the presence of pathogenic bacteria in dogs or cats, and in particular to limit the formation or adhesion of biofilm. The pathogenic bacteria are in particular *Staphylococcus aureus* and/or *Staphylococcus pseudintermedius*.

TABLE 1

| Compound Trade name (company) | Compound INCI name | % Compound in the composition |
|---|---|---|
| Water | AQUA | QS 100 |
| | PRESERVATIVE | qs |
| | PANTHENOL | 0.5 |
| Tego ® Betain 810 (Evonik) | CAPRYLAMIDOPROPYL BETAINE/CAPRAMIDOPROPYL BETAINE in aqueous solution at 35.5% MA | 4 |
| Jaguar ® Excel (Solvay) | GUAR HYDROXYPROPYLTRIMONIUM CHLORIDE at 95% MA with water | 0.1 |
| Ophytrium (Ceva) | *OPHIOPOGON JAPONICUS* ROOT EXTRACT at 71% MA with maltodextrin | 0.75 |
| Pentavitin ® (DSM) | SACCHARIDE ISOMERATE in aqueous solution at 50% MA | 1 |

TABLE 2

| Compound Trade name (company) | Compound INCI name | % Compound in the composition |
|---|---|---|
| Water | AQUA | QS 100 |
| | CHLOREXIDINE DIGLUCONATE | 3 |
| | PRESERVATIVE | qs |
| | PANTHENOL | 0.5 |
| Oramix ® CG110 (Seppic) | CAPRYLYL/CAPRYL GLUCOSIDE (in aqueous solution at 60% MA) | 2 |
| Jaguar ® Excel (Solvay) | GUAR HYDROXYPROPYLTRIMONIUM CHLORIDE at 95% MA with water | 0.1 |
| Ophytrium (Ceva) | *OPHIOPOGON JAPONICUS* ROOT EXTRACT at 74% MA with maltodextrin | 0.5 |
| Pentavitin ® (DSM) | SACCHARIDE ISOMERATE in aqueous solution at 50% MA | 0.1 |

TABLE 3

| Compound Trade name (company) | Compound INCI name | % Compound in the composition |
|---|---|---|
| Water | AQUA | QS 100 |
| | PRESERVATIVE | qs |
| | PANTHENOL | 0.5 |
| Oramix ® L30 (Seppic) | SODIUM LAUROYL SARCOSINATE (in aqueous solution at 30% MA) | 2 |
| Ophytrium (Ceva) | OPHIOPOGON JAPONICUS ROOT EXTRACT at 74% MA with maltodextrin | 0.5 |
| Pentavitin ® (DSM) | SACCHARIDE ISOMERATE in aqueous solution at 50% MA | 1 |

What is claimed is:

1. A non-rinsed veterinary composition comprising an active ingredient obtained from *Ophiopogon japonicus*, panthenol and saccharide isomerate, wherein the composition comprises from 0.3 to 0.8 wt % panthenol and from 0.1 to 1 wt % saccharide isomerate, with respect to the total weight of the composition.

2. The veterinary composition according to claim 1, comprising at least 0.1 wt. % active agent obtained from *Ophiopogon japonicus* with respect to the total weight of the composition.

3. The veterinary composition according to claim 1, comprising between 0.3 wt % and 0.9 wt % saccharide isomerate, with respect to the total weight of the composition.

4. The veterinary composition according to claim 1, wherein the composition is in the form selected from a lotion, a gel, a cream, or a mousse.

5. The veterinary composition according to claim 1, wherein the composition comprises one or more surfactant (s) selected from amphoteric surfactants of the betaine type, carboxylic anionic surfactants, alkyl (poly) glucoside non-ionic surfactants, and mixtures thereof.

6. The veterinary composition according to claim 5, wherein the surfactant is selected from sodium lauroyl sarcosinate, capryl/capramidopropyl betaine, caprylyl/capryl glucoside, or mixtures thereof.

7. The veterinary composition according to claim 5, wherein the surfactant is present in amounts of from 0.1 to 10 wt. %, with respect to the total weight of the composition.

8. The veterinary composition according to claim 1, wherein the composition further comprises cationic galactomannan gums.

9. The veterinary composition according to claim 1, wherein the composition is provided in the form of a mousse.

10. A method for treating the skin and/or the coat of a non-human mammal by applying the composition according to claim 1 to the skin and/or the coat of said mammal.

11. A method for reducing and/or preventing the formation and/or the adhesion of biofilms of pathogenic bacteria, or for reducing the presence of pathogenic bacteria on the skin or the coat, in a non-human mammal by applying the veterinary composition according to claim 1 to the skin or the coat of a non-human mammal.

12. The method according to claim 11, characterized in that the pathogenic bacteria are selected from *Staphylococcus aureus* and/or *Staphylococcus pseudintermedius*.

13. A veterinary treatment device for treating the skin and/or the coat of a non-human mammal, comprising:

a veterinary composition according to claim 5; and a mousse dispenser, allowing distribution of said composition in the form of a mousse.

* * * * *